US006535828B1

(12) United States Patent
Furukawa et al.

(10) Patent No.: US 6,535,828 B1
(45) Date of Patent: Mar. 18, 2003

(54) METHOD AND APPARATUS FOR VISUALIZING ELASTIC WAVE PROPAGATION IN A SOLID SUBSTANCE

(75) Inventors: Takashi Furukawa, Kanagawa-ken (JP); Hiroshi Yoneyama, Kanagawa-ken (JP); Yukihiko Horii, Kanagawa-ken (JP); Nobuo Uesugi, Kanagawa-ken (JP)

(73) Assignee: Japan Power Engineering and Inspection Corporation, Tokyo (JP)

( * ) Notice: Subject to any disclaimer, the term of this patent is extended or adjusted under 35 U.S.C. 154(b) by 29 days.

(21) Appl. No.: 09/695,911

(22) Filed: Oct. 26, 2000

(30) Foreign Application Priority Data

Apr. 12, 2000 (JP) ........................................ 2000-111003

(51) Int. Cl.[7] .......................... G01F 17/00; G01F 23/00; G01L 7/00; G01N 11/00; G06F 19/00
(52) U.S. Cl. ....................................................... 702/56
(58) Field of Search .............................. 702/35, 38, 40, 702/56; 356/237, 493, 502; 73/655

(56) References Cited

U.S. PATENT DOCUMENTS

| | | | | |
|---|---|---|---|---|
| 4,649,750 A | * | 3/1987 | Cantrell et al. | ............... 73/1.82 |
| 5,623,307 A | * | 4/1997 | Kotidis et al. | ............... 356/432 |
| 6,092,420 A | * | 7/2000 | Kimura et al. | ................. 73/599 |

* cited by examiner

Primary Examiner—John Barlow
Assistant Examiner—Anthony Dougherty

(74) Attorney, Agent, or Firm—Sughrue Mion, PLLC

(57) ABSTRACT

A method and an apparatus for visualizing an elastic wave propagation in a solid substance can be applied to a subject substance which is any one of a transparent body and an opaque body, and can detect SV waves (transverse waves) and SH waves (transverse waves) in elastic wave motion modes, and longitudinal waves, surface waves, and creeping waves. The visualization method comprises the steps of: generating elastic waves in a solid substance in response to electric signals; measuring a quantity of stress change in the solid substance in connection with elastic waves propagation in the solid substance; synchronizing a transmission timing of the electric signals with a measurement timing of the stress change; carrying out measurement while scanning a sensor; and imaging wave fronts of the elastic waves propagated in the solid substance by synchronously indicating the stress change as a function of time. The visualization apparatus comprises an elastic wave generator (8) for generating elastic waves in a solid substance (9) in response to an electric signals; an electric signal transmitter (7) for transmitting electric signals to the elastic wave generator (8); a sensor (1) for measuring elastic waves propagated in the solid substance; a sensor scanner (3) for controlling a scanning position of said sensor; a detected-signal recorder (2) for receiving and recording detected-signals from the sensor (1); a synchronizing circuit (10) for sending the detected-signals from the sensor (1) to the recorder (1) in synchronization with timing signals from the sensor scanner (3) and electric signal transmitter (7); and an elastic wave stress distribution display (4) for imaging stress distribution signals of the detected-signals from the detected-signal recorder (2).

15 Claims, 7 Drawing Sheets

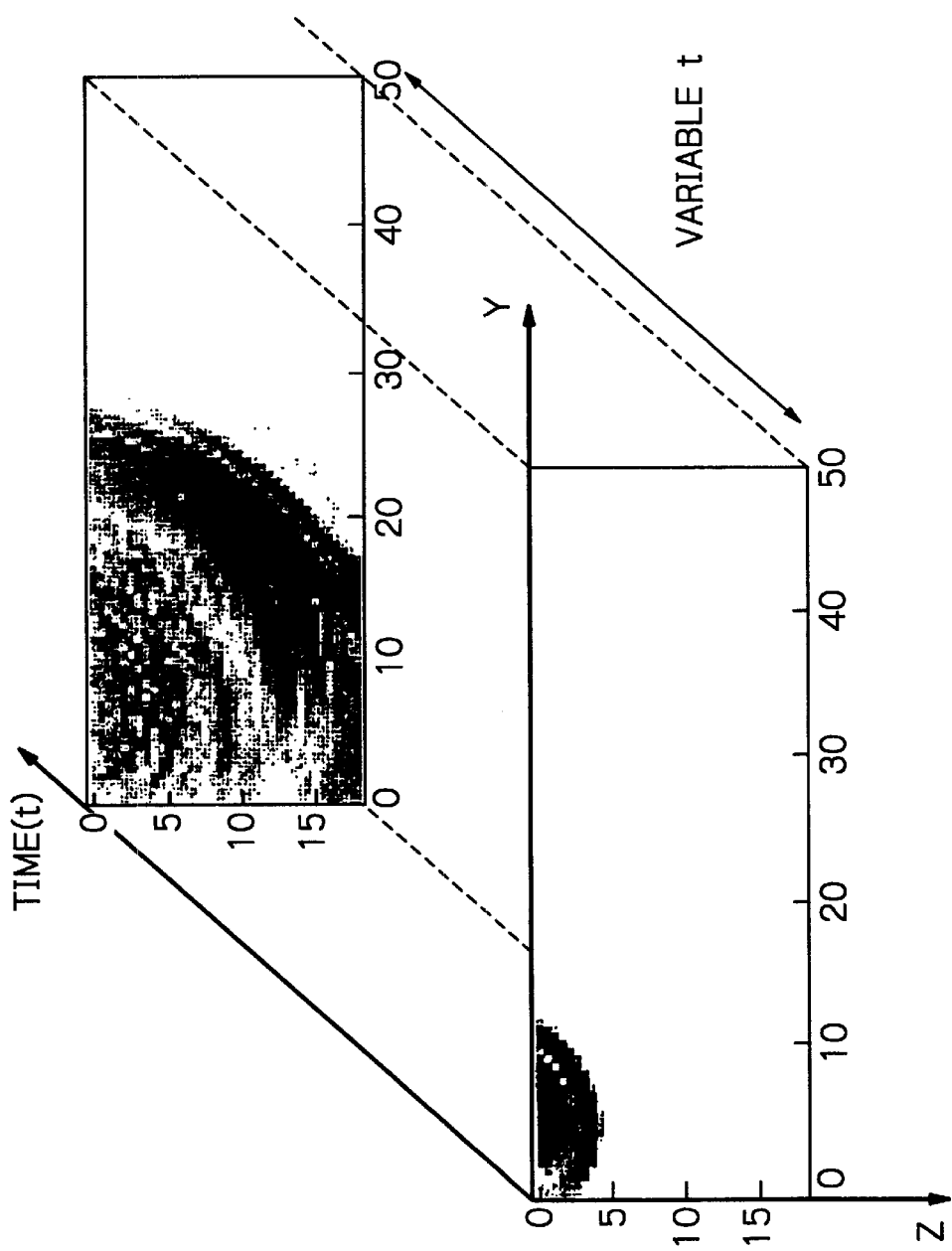

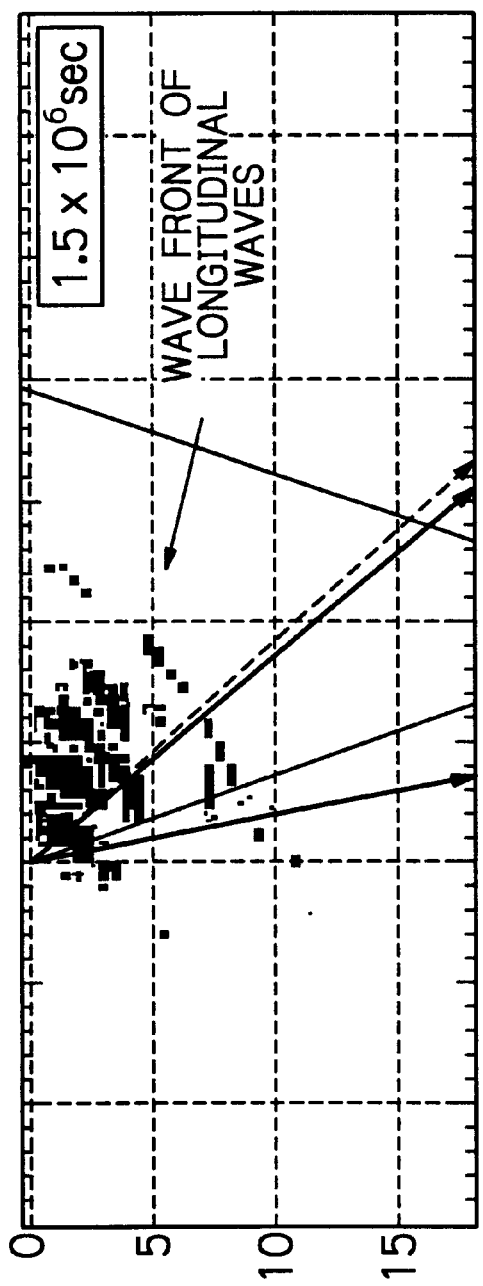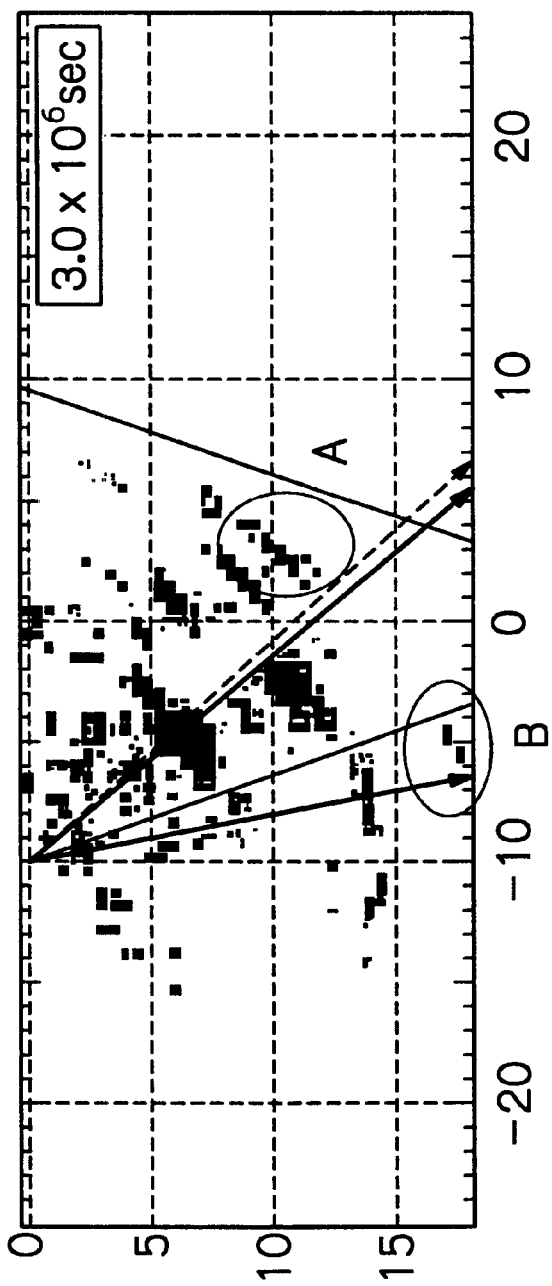
Fig. 6A
Fig. 6B

METHOD AND APPARATUS FOR VISUALIZING ELASTIC WAVE PROPAGATION IN A SOLID SUBSTANCE

BACKGROUND OF THE INVENTION

This invention relates to a method and an apparatus for visualizing elastic waves which propagate in a solid substance. Here, a solid substance means an elastic body (for example, metal, concrete, synthetic resin, glass, or the like). An elastic wave means a wave of elastic oscillation which propagates in the elastic body.

Heretofore, a typical method for visualizing elastic waves in the solid substance included a visualization method for the elastic waves which utilizes a principle of photo-elasticity and a visualization method which measures a displacement of an exterior of the solid substance by utilizing a laser displacement meter.

First of all, the visualization method for the elastic waves which utilizes the principle of photo-elasticity is a method which measures a stress generated in the solid substance upon elastic wave propagation therein in accordance with the principle of photo-elasticity. The first method can visualize a behavior of a wave front of an instantaneous elastic wave by synchronizing a timing of elastic wave radiation with a timing of flashing a stroboscopic lamp. It is also possible to visualize a behavior of elastic wave propagation by varying the timings.

The second visualization method which measures a displacement of an exterior of the solid substance by utilizing a laser displacement meter is a method which measures a displacement of the solid substance upon elastic wave propagation on a surface or an interior of the solid substance from the outside by means of the laser displacement meter. The second method can visualize a behavior of a wave front of an elastic wave by synchronizing a timing of elastic wave radiation with a timing of measuring the displacement and by measuring a displacement distribution while scanning a sensor.

The first photo-elasticity method is limited to a subject substance which is a transparent body having a photo-elasticity effect (for example, glass, synthetic resin, or the like) and cannot measure a transverse wave (SH wave). The second laser method is limited to a substance which is an opaque body since a laser must be reflected and cannot detect transverse waves (SV waves) and surface waves.

Accordingly, an object of the present invention is to provide a method and an apparatus for visualizing an elastic wave propagation in a solid substance, that can be applied to a subject substance which is any one of a transparent body and an opaque body and that can detect SV waves (transverse waves) and SH waves (transverse waves) in elastic wave motion modes, and longitudinal waves, surface waves, and creeping waves.

Here, a longitudinal wave means a progressive wave in which an oscillating direction of a medium particle coincides with an oscillating direction of propagation. A transverse wave means a progressive wave in which an oscillating direction of a medium particle is perpendicular to an oscillating direction of propagation. An SV wave means a wave (a kind of transverse wave) generated by bringing a longitudinal wave into incidence into a specimen. An SH wave means a wave (a kind of transverse wave) generated by applying to a specimen an external force which horizontally rubs a surface of the specimen. A creeping wave is generated by bringing a longitudinal wave into incidence into a specimen at a critical angle of a longitudinal wave (a first critical angle) and is a longitudinal wave which progresses straightly along a surface of a specimen.

SUMMARY OF THE INVENTION

In order to achieve the above object, a method for visualizing elastic wave propagation in a solid substance in accordance with the present invention comprises the following steps of:

(1) generating elastic waves in a solid substance in response to electric signals;
(2) measuring a quantity of stress change in the solid substance in connection with elastic wave propagation in the solid substance;
(3) synchronizing a transmission timing of the electric signals with a measurement timing of the stress change;
(4) carrying out measurement while scanning a sensor; and
(5) imaging wave fronts of the elastic waves propagated in the solid substance by synchronously indicating the stress change as a function of time.

The visualization method of the present invention may further comprises the steps of (6) delaying the imaging step; and (7) imaging a propagating condition in the elastic waves propagated in the solid substance by changing a delay time.

The quantity of stress change can be detected as a voltage change by a voltage sensor. Also, the stress change can be detected as a displacement in the solid substance by an electromagnetic sensor.

The visualization method can be applied to a ultrasonic flaw detecting method for detecting a flaw in a metal material by transmitting ultrasonic waves into a welded portion of austenitic steel (for example, an austenitic stainless steel, a nickel base high alloy, or the like). Also, a condition of elastic wave propagation in a metal material can be simulated by applying the visualization method to a transparent elastic body.

An apparatus for carrying out the method for visualizing elastic wave propagation in a solid substance comprises: an elastic wave generator for generating elastic waves in a solid substance in response to electric signals; an electric signal transmitter for transmitting electric signals to the elastic wave generator; a sensor for measuring elastic waves propagated in the solid substance; a sensor scanner for controlling a scanning position of the sensor; a detected-signal recorder for receiving and recording detected-signals from the sensor; a synchronizing circuit for sending the detected-signals from the sensor to said recorder in synchronization with timing signals from the sensor scanner and electric signal transmitter; and an elastic wave stress distribution display for imaging stress distribution signals of the detected-signals from the detected-signal recorder.

The visualization apparatus may further comprise a delay circuit for sending delay time signals to the elastic wave stress distribution display. In the visualization apparatus, a wedge member may be attached to a distal end of the sensor in order to measure a small region of area.

The visualization apparatus can be applied to an ultrasonic flaw detecting method for detecting a flaw in a metal material by transmitting an ultrasonic wave into a welded portion of an austenitic steel (for example, an austenitic stainless steel, a nickel base high alloy, or the like). Also, a condition of elastic wave propagation in a metal material can be simulated by applying the visualization method to a transparent elastic body.

BRIEF DESCRIPTION OF THE DRAWINGS

The foregoing and other features of the present invention will become apparent to one skilled in the art to which the present invention relates upon consideration of the invention with reference to the accompanying drawings, wherein:

FIG. 5 is an explanatory view of a detected-signal image visualized in accordance with the visualization method of the present invention;

FIGS. 6A and 6B are visualized images in an austenitic base stainless steel obtained by applying the visualization method of the present invention to an ultrasonic flaw detecting method;

DETAILED DESCRIPTION OF THE PREFERRED EMBODIMENTS

Figure 1:
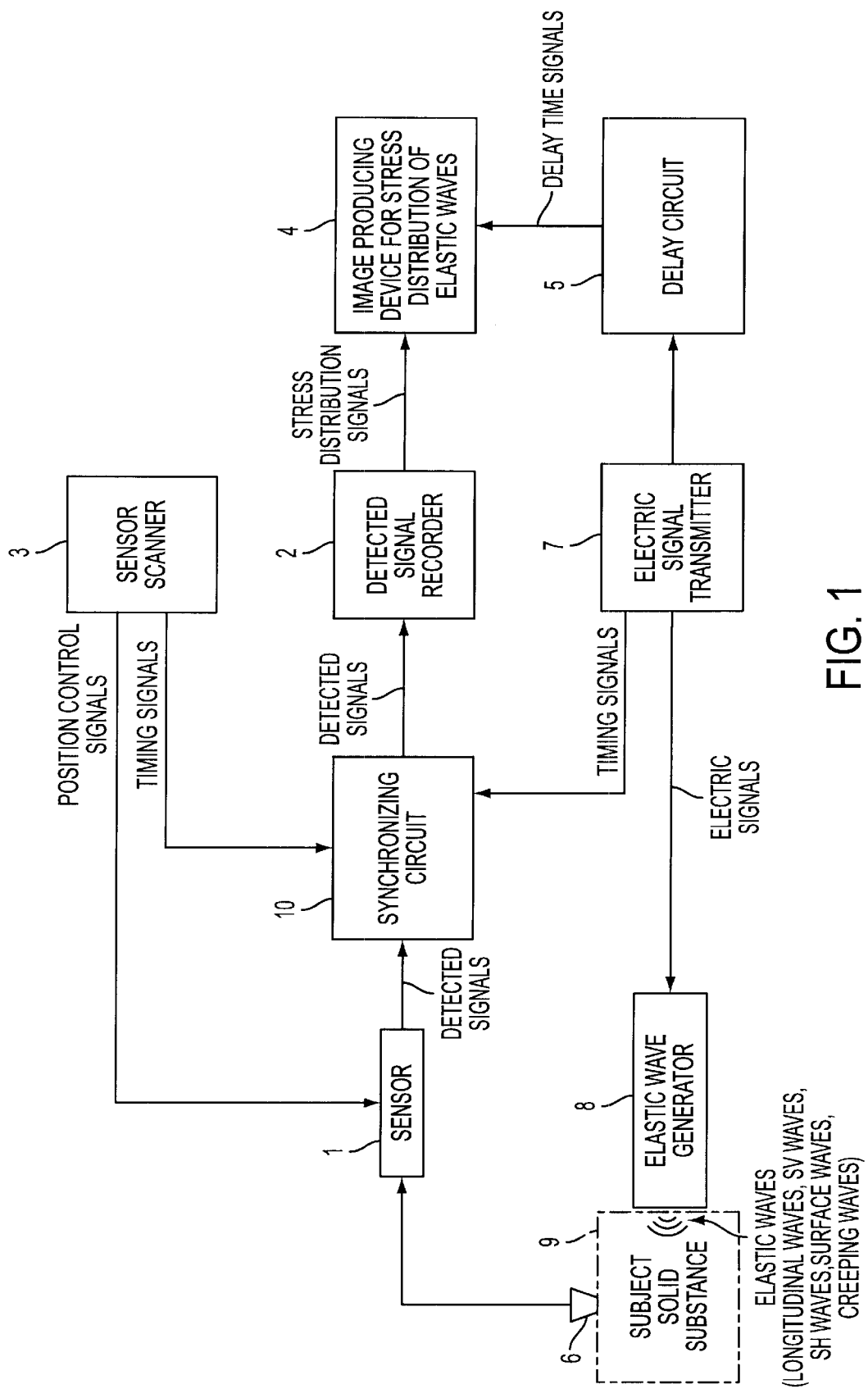
FIG. 1 is a schematic block diagram of an apparatus for visualizing elastic wave propagation in a solid substance in accordance with the present invention.

Referring now to the drawings, embodiments of a method and an apparatus for visualizing elastic wave propagation in a solid substance in accordance with the present invention will be explained bellow.

First of all, by referring now to FIG. 1, an embodiment of an apparatus for visualizing elastic wave propagation in a solid substance is described. The apparatus for visualizing elastic wave propagation in a solid substance in accordance with the present invention comprises: an elastic wave generator 8 for generating elastic waves in a solid substance 9 in response to electric signals; an electric signal transmitter 7 for transmitting electric signals to the elastic wave generator 8; a sensor 1 for measuring elastic waves propagated in the solid substance; a sensor scanner 3 for controlling a scanning position of the sensor; a detected-signal recorder 2 for receiving and recording detected-signals from the sensor 1; a synchronizing circuit 10 for sending the detected-signals from the sensor 1 to the recorder 2 in synchronization with timing signals from the sensor scanner 3 and electric signal transmitter 7; and an elastic wave stress distribution display 4 for imaging stress distribution signals of the detected-signals from the detected-signal recorder.

The visualization apparatus may further comprises a delay circuit 5 for sending a delay time signal to the elastic wave stress distribution display 4.

Figure 4A:
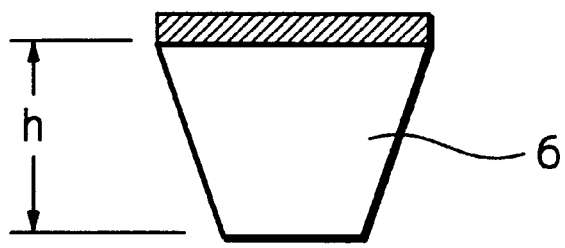
FIG. 4A is a side elevational view of a wedge member to be mounted on a distal end of a sensor.
Figure 4B:
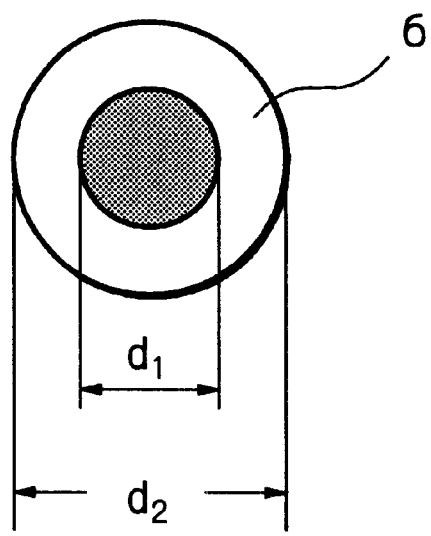
FIG. 4B is a bottom view of the wedge member shown in FIG. 4A.

The subject solid substance 9 is an elastic body (for example, metal, concrete, synthetic resin, glass, or the like). The elastic wave generator 8 may be a probe to be utilized in an ultrasonic flaw detector for detecting a flaw. The probe converts an electrical oscillation into a mechanical oscillation and propagates elastic waves into an elastic substance. It is possible to alter a wave motion mode in an elastic substance by changing a slant angle of an oscillator in the probe. The sensor 1 may be a voltage sensor by which stress change is detected as voltage change, or an electromagnetic sensor by which stress change is detected as a displacement in the solid substance. In order to measure a small region of area, a wedge member 6 shown in FIGS. 4A and 4B is preferably attached to a distal end of the sensor 1 (see FIG. 1). The wedge member 6 shown in FIGS. 4A and 4B is made of a synthetic resin (preferably, polystyrene resin) and formed into a cone shape. An example of dimensions of the wedge member 6 is preferably 8.0 mm in height (FIG. 4A), 2.0 mm in top small diameter $d_1$, and 5.0 mm in bottom large diameter $d_2$ (FIG. 4B).

Next, an embodiment of a method for visualizing elastic wave propagation in a solid substance in accordance with the present invention will be described by referring to FIGS. 1, 2, 3, and 5. The visualization method of the present invention comprises the following steps of:

(1) generating an elastic wave in a subject solid substance 9 in response to an electric signal from an electric signal transmitter 7;

(2) measuring a quantity of stress change in the solid substance 9 in connection with elastic wave propagation in the solid substance 9 by means of a sensor 1;

(3) synchronizing a transmission timing of the electric signals from the electric signal transmitter 7 with a measurement timing of the stress change from a sensor scanner 3 to the sensor 1 by means of a synchronizing circuit 10;

(4) carrying out measurement while scanning the sensor 1 by means of the sensor scanner 3 and recording detected-signals in a detected-signal recorder 2 (see FIG. 3); and (5) imaging wave fronts of the elastic waves propagated in the solid substance 9 by means of an elastic wave stress distribution display 4 so that stress distribution signals of the detected wave from the detected-signal recorder 2 is synchronously indicated as a function of time (see FIG. 5).

The visualization method may further comprise the steps of: (6) delaying the imaging step by sending delay time signals from a delay circuit 5 to the elastic wave stress distribution display 4 (see FIG. 3); and (7) imaging a propagating condition in the elastic waves propagated in the solid substance 9 by changing a delay time (see FIG. 5).

Figure 2:
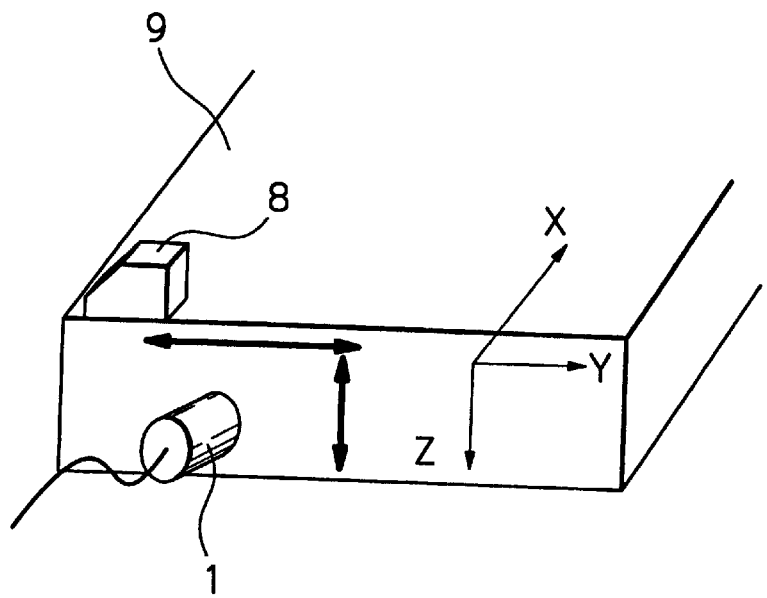
FIG. 2 is a perspective view of an elastic wave generator and a sensor in the apparatus of the present invention, illustrating a relationship of an attaching position between the elastic wave generator and the sensor on a solid substance.

The above visualization method will be explained in more detail. As shown in FIG. 2, it is assumed that the subject solid substance 9 is a rectangular body having orthogonal coordinate axes X, Y, and Z. The sensor 1 is disposed on the Y-Z plane and is scanned in the Y axis direction and the Z axis direction by the sensor scanner 3. The elastic wave generator (probe) 8 is disposed on the X-Y plane.

Figure 3:
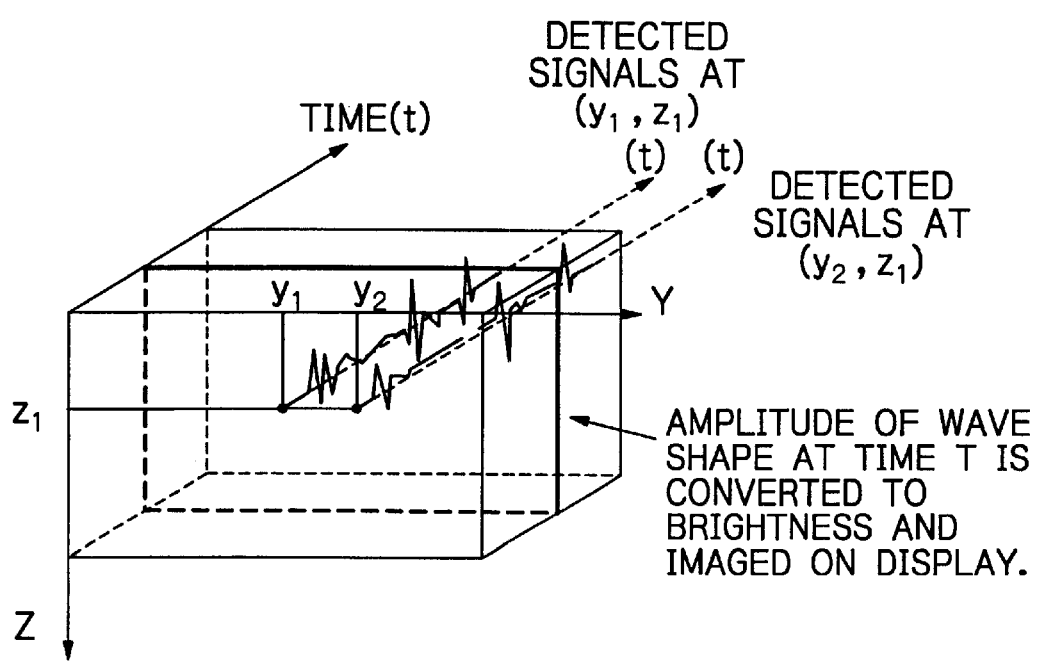
FIG. 3 is an explanatory view illustrating a principle of a method for visualizing elastic wave propagation in a solid substance in accordance with the present invention.

Under this condition, FIG. 3 illustrates a wave shape of indicating detected-signals as a function of a time t when the sensor 1 is scanned to positions of coordinates $(y_1, z_1)$ and $(y_2, z_2)$, respectively. In the visualization method, amplitude of a wave shape of the detected-signals is imaged in color indication. That is, the amplitude of the wave shape at a time t is converted to a luminance and imaged. When the wave shapes at detecting positions (y, z) are assembled and imaged, wave fronts after a time t are indicated. When changing the time t and imaging, a behavior of elastic wave propagation can be indicated (see FIG. 5).

The visualization method can be applied to an ultrasonic flaw detecting method for detecting a flaw in a metal material by transmitting ultrasonic waves into a welded portion of an austenitic steel (for example, an austenitic stainless steel, a nickel base high alloy, or the like). Also, a condition of elastic wave propagation in a metal material can be simulated by applying the visualization method to a transparent elastic body. As an application of the visualization method, an embodiment of ultrasonic flaw detection will be described by referring to FIGS. 6 to 8. Table 1 shows welding conditions of specimens to be used for measurement.

TABLE 1

Preparing Condition of Welding Specimens

| Welding Method | Welding Position | Heat Inputs (kJ/mm) | Oxygen Contents (ppm) | Crystal Diameters ($\mu$m) | Notes (Aims) |
|---|---|---|---|---|---|
| GTAW | Flat | 1.9 | 30 | — | V-groove Quantity of Heat Input Comparison |
| GTAW | Flat | 3.6 | 30 | — | |
| Submerged Arc Welding | Flat | 3.5 | 350 | — | of V-groove and GTA |
| Cladd welding with SAW | Flat | 5.7 | 350 | — | Quantity of Heat Input |
| Cladd welding with SAW | Flat | 10.0 | 350 | 400–800 | Quantity of Heat Input |
| Electron Beam Welding | Flat | (1 pass) | 20 | 50–100 | Size of Bead Width |
| Electron Beam Welding | Flat | (6 passes) | 20 | — | Size of Bead Width |

A base material was a SUS 304 steel having a thickness of 20 mm. Propagation of ultrasonic waves was investigated by altering conditions of a welding method and a heat input or the like. Also, in order to investigate a relationship between sizes of welded metallographic structures and propagation of ultrasonic waves, anisotropy of acoustic velocities in cladding welding metals having uniform growth directions and different grain sizes and in electron beam welding metals was measured. In accordance with a double probe technique, a probe (8) for transmission was placed on a top surface (X-Y plane) of a specimen (9) and a probe (1) for receiving was scanned to measure an out-of-plane displacement on a side surface (Y-Z plane). A behavior of propagation of ultrasonic wave pulses was visualized by synchronously indicating received wave shapes in a computer (2, 4, 5, 10). Also, a receiving probe (1) was disposed on a rear surface of the specimen (9) and a behavior of propagation of ultrasonic waves in the welds in connection with a transmission method was measured.

Figure 8A:
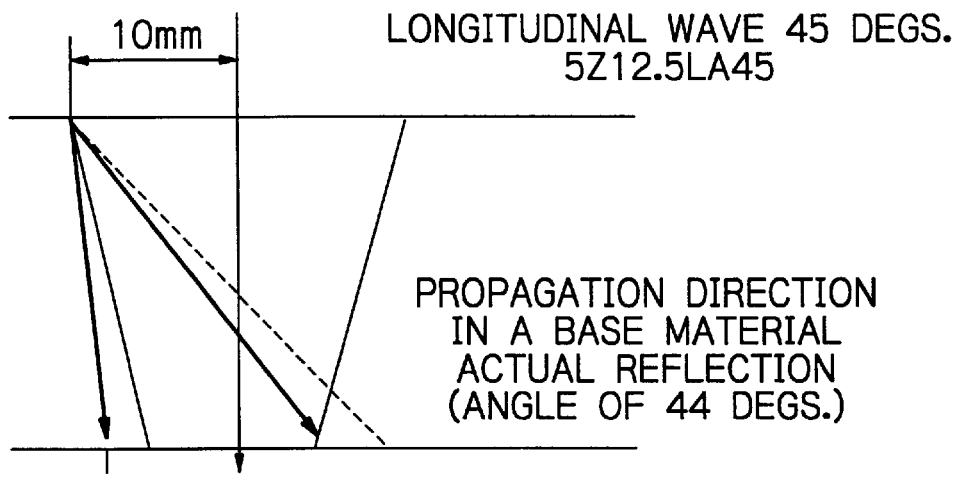
FIG. 8A is an explanatory view of a longitudinal wave radiation in a conventional transmission method.
Figure 8B:
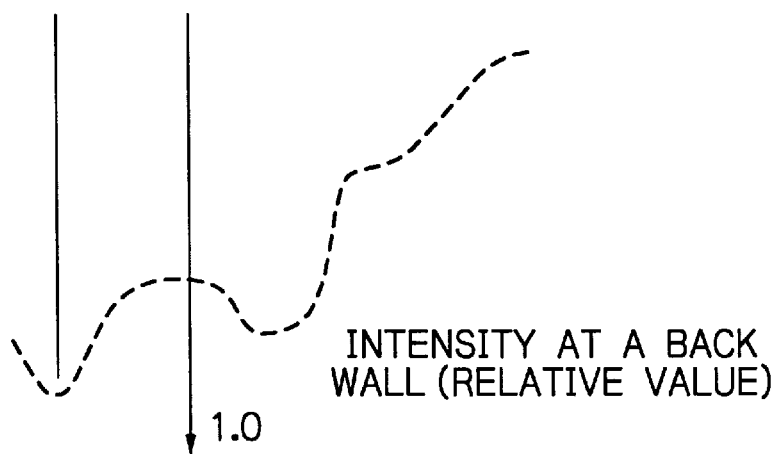
FIG. 8B is a graph illustrating a result of measuring longitudinal wave propagation.

FIG. 8A shows a presumptive propagation direction of ultrasonic waves while FIG. 8B shows a result of the transmission method. In FIG. 8B, an axis of abscissas illustrates a position of a receiving probe while an axis of ordinates illustrates amplitude standardized by a maximum value.

FIGS. 6A and 6B show front waves of ultrasonic waves (longitudinal waves) which are measured in areas from Y=−25 mm to 25 mm and from Z=0 mm to 19 mm by using the apparatus of the present invention and are indicated by a gray scale with respect to displacements (amplitudes) at an interval of time of 1.5 $\mu$sec. after incidence. It will be apparent from FIG. 6B that the amplitudes in areas A and B become great and well accord with the results of the transmission method.

Figure 7A:
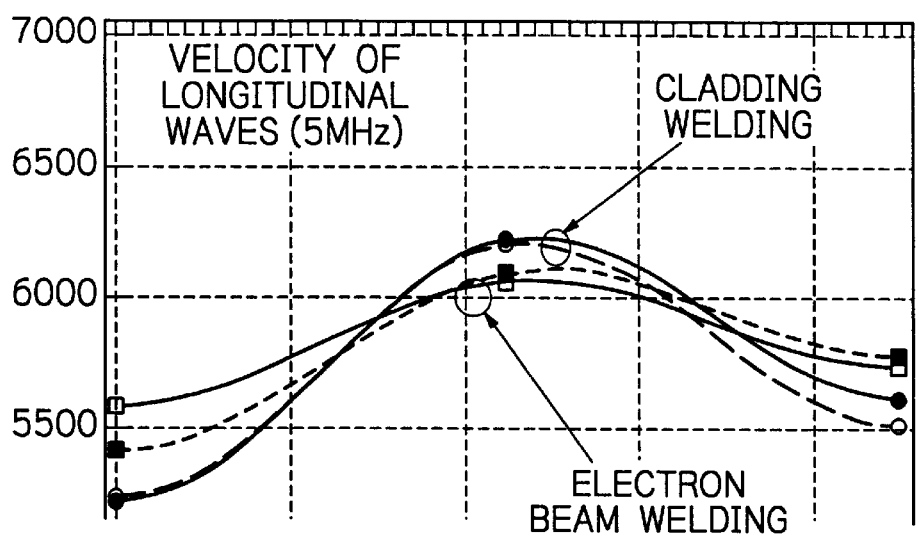
FIGS. 7A and 7B are graphs illustrating results of measuring distributions of acoustic velocity in a cladding welding metal and an electron beam welding metal.
Figure 7B:
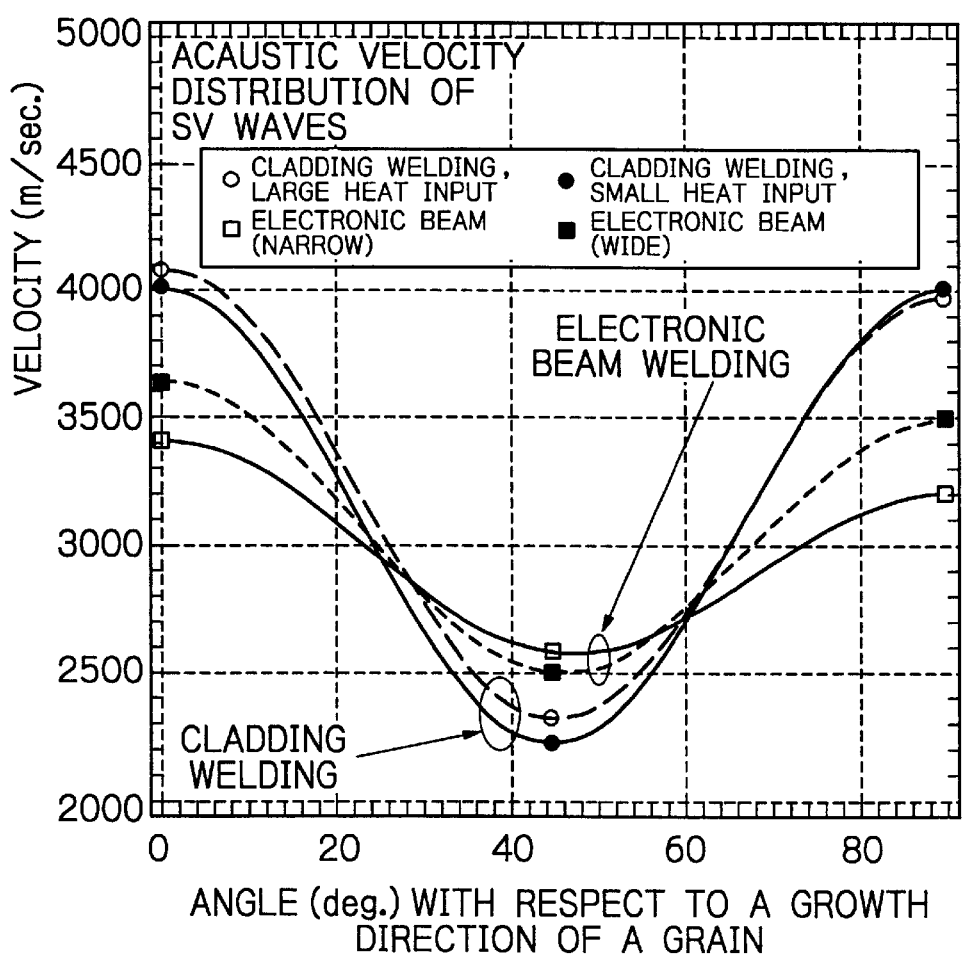

Next, anisotropy of acoustic velocities in cladding metals having a substantially same configuration of grain growth and different grain sizes and in electron beam welded metals was measured. The results were shown in FIGS. 7A and 7B. An axis of abscissas indicates a progressive angle of ultrasonic waves while an axis of ordinates indicates an acoustic velocity. FIG. 7A illustrates an acoustic velocity distribution of longitudinal waves (5 MHz) while FIG. 7B illustrates an acoustic velocity distribution of transverse waves (SV waves) (3.5 MHz). Consequently, it will be seen that the anisotropy in the electron beam welding metals is smaller than that in the cladding welding metals. Since an observation of grains suggests that the electron beam welding metals have small, uniformized, and uniform crystal bearing grains, there will be a possibility of improving a propagation performance of ultrasonic waves by fining and uniformizing a grain size.

Heretofore, it was difficult to effect ultrasonic flaw detecting in an austenitic steel (for example, stainless steel, nickel base high alloy, or the like). A conventional flaw detection technique has been much developed mainly in an aspect of inspection (ultrasonic flaw detection). On the other hand, in an aspect of welding, a research of welding in consideration of a propagation character of ultrasonic waves has focused a magnetic agitation. However, a relationship between a welding condition and a propagation character of ultrasonic waves has not been resolved quantitatively. The present invention can comply with the above problems.

According to the present invention, it is possible to effect visualization whether a subject solid substance is transparent or opaque, and also possible to visualize a longitudinal wave, a creeping wave, a transverse wave (SH wave, SV wave), surface wave in an elastic wave motion mode. The visualization method and apparatus of the present invention can evaluate a propagation character of ultrasonic waves in ultrasonic flaw detection and simulate a propagation character of elastic waves in an opaque body by using a transparent body.

From the above description of the invention, those skilled in the art will perceive improvements, changes and modifications. Such improvements, changes and modifications within the skill of the art are intended to be covered by the appended claims.

The entire disclosure of Japanese Patent Application No. HEI 12 - 111003 (2000) filed on Apr. 12, 2000 including specification, claims, drawings and summary is incorporated herein by reference in its entirety.

What is claimed is:

1. A method for visualizing elastic wave propagation in a solid substance, comprising the steps of:

(1) generating elastic waves in a solid substance by an elastic wave generator in response to electric signals;

(2) measuring a quantity of stress change in the solid substance in connection with elastic wave propagation in the solid substance by a sensor;

(3) synchronizing a transmission timing of the electric signals with a measurement timing of the stress change;

(4) carrying out measurement while scanning said sensor on the surface of said solid substance perpendicular to the surface of said solid surface on which said elastic wave generator is disposed; and (5) imaging wave fronts of the elastic waves propagated in the solid substance by synchronously indicating the stress change as a function of time.

2. A method for visualizing elastic wave propagation in a solid substance, comprising the steps of:
   (1) generating elastic waves in a solid substance by an elastic an elastic wave generator in response to electric signals;
   (2) measuring a quantity of stress change in the solid substance in connection with elastic wave propagation in the solid substance by a sensor;
   (3) synchronizing a transmission timing of the electric signals with a measurement timing of the stress change;
   (4) carrying out measurement while scanning said sensor on the surface of said solid substance perpendicular to the surface of said solid surface on which said elastic wave generator is disposed;
   (5) imaging wave fronts of the elastic waves propagated in the solid substance by synchronously indicating the stress change as a function of time;
   (6) delaying said imaging step; and
   (7) imaging a propagating condition in the elastic waves propagated in the solid substance by changing a delay time.

3. A method according to claim 1 or 2, wherein said stress change is detected as a voltage change by a voltage sensor.

4. A method according to claim 1 or 2, wherein said stress change is detected as a displacement in the solid substance by an electromagnetic sensor.

5. A ultrasonic flaw detecting method for detecting a flaw in an austenitic stainless steel weld, comprising the steps of: transmitting ultrasonic waves into an austenitic stainless steel weld; and utilizing a method according to claim 1 or 2.

6. A visualization method for simulating a condition of elastic wave propagation in a metal material by applying a method according to claim 1 or 2 to a transparent elastic body.

7. An apparatus for visualizing elastic wave propagation in a solid substance, comprising:
   an elastic wave generator (8) for generating elastic waves in a solid substance (9) in response to electric signals;
   an electric signal transmitter (7) for transmitting electric signals to said elastic wave generator (8);
   a sensor (1) disposed on the surface of said solid substance perpendicular to the surface of said solid surface on which said elastic wave generator is disposed for measuring elastic waves propagated in said solid substance;
   a sensor scanner (3) for controlling a scanning position of said sensor;
   a detected-signal recorder (2) for receiving and recording a detected-signals from said sensor (1);
   a synchronizing circuit (10) for sending said detected-signals from said sensor (1) to said recorder (1) in synchronization with timing signals from said sensor scanner (3) and electric signal transmitter (7); and
   an elastic wave stress distribution display (4) for imaging stress distribution signals of the detected-signals from said detected-signal recorder (2).

8. The visualization apparatus according to claim 7, wherein a conical wedge member for measuring a prescribed area of said solid substance is attached to a distal end of said sensor.

9. The visualization apparatus according to claim 8, wherein said conical wedge member has a height of 8 mm, a top diameter of 2 mm and a bottom diameter of 5 mm.

10. The visualization apparatus according to claim 7, wherein said solid substance is one of opaque and transparent.

11. The visualization apparatus according to claim 7, wherein said elastic waves are selected from the group consisting of longitudinal waves, SV waves, SH waves, surface waves, and creeping waves.

12. An apparatus for visualizing elastic wave propagation in a solid substance, comprising:
   an elastic wave generator (8) for generating elastic waves in a solid substance (9) in response to electric signals;
   an electric signal transmitter (7) for transmitting electric signals to said elastic wave generator (8);
   a sensor (1) disposed on the surface of said solid substance perpendicular to the surface of said solid surface on which said elastic wave generator is disposed for measuring an elastic wave propagated in said solid substance;
   a sensor scanner (3) for controlling a scanning position of said sensor;
   a detected-signal recorder (2) for receiving and recording detected-signals from said sensor (1);
   a synchronizing circuit (10) for sending said detected-signals from said sensor (1) to said recorder (1) in synchronization with timing signals from said sensor scanner (3) and electric signal transmitter (7);
   an elastic wave stress distribution display (4) for imaging a stress distribution signal of the detected-signals from said detected-signal recorder (2); and
   a delay circuit (5) for sending delay time signals to said elastic wave stress distribution display (4).

13. A visualization apparatus according to claim 7 or 12, wherein a wedge member (6) for measuring a small region of area is attached to a distal end of said sensor (1).

14. A ultrasonic flaw detecting apparatus for detecting a flaw in an austenitic stainless steel weld, wherein ultrasonic waves are transmitted into an austenitic stainless steel weld by utilizing a method according to claim 7 or 12.

15. A visualization apparatus for simulating a condition of elastic wave propagation in a metal material by applying an apparatus according to claim 7 or 12 to a transparent elastic body.

* * * * *